United States Patent
O'Neill et al.

(10) Patent No.: US 11,673,127 B2
(45) Date of Patent: Jun. 13, 2023

(54) CATALYST FORMULATION FOR METHANOL CONVERSION CATALYSTS

(71) Applicant: ExxonMobil Technology and Engineering Company, Annandale, NJ (US)

(72) Inventors: Brandon J. O'Neill, Lebanon, NJ (US); Scott J. Weigel, Allentown, PA (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/807,500

(22) Filed: Mar. 3, 2020

(65) Prior Publication Data
US 2020/0290027 A1 Sep. 17, 2020

Related U.S. Application Data (60) Provisional application No. 62/818,339, filed on Mar. 14, 2019.

(51) Int. Cl.
C07C 1/20 (2006.01)
B01J 37/06 (2006.01)
(Continued)

(52) U.S. Cl.
CPC ............. B01J 29/703 (2013.01); B01J 21/04 (2013.01); B01J 37/0072 (2013.01); B01J 37/06 (2013.01);
(Continued)

(58) Field of Classification Search
CPC ........................................................ B01J 37/06
See application file for complete search history.

(56) References Cited

U.S. PATENT DOCUMENTS

| 3,354,078 A | 11/1967 | Miale et al. |
| 3,702,886 A | 11/1972 | Argauer et al. |

(Continued)

FOREIGN PATENT DOCUMENTS

| CN | 1151722 A | 6/1997 |
| CN | 105814009 A | 7/2016 |

(Continued)

OTHER PUBLICATIONS

Zhang et al. "Protective desilication of highly siliceous H-ZSM-5 by sole tetraethylammonium hydroxide for the methanol to propylene (MTP) reaction" RCE Advances. 2018, 8, 37842-37854 (Year: 2018).*

(Continued)

*Primary Examiner* — Philip Y Louie
*Assistant Examiner* — Alyssa L Cepluch
(74) *Attorney, Agent, or Firm* — Shook, Hardy & Bacon L.L.P.

(57) ABSTRACT

Methods are provided for formulation of catalysts with improved catalyst exposure lifetimes under oxygenate conversion conditions. In various additional aspects, methods are described for performing oxygenate conversion reactions using such catalysts with improved catalyst exposure lifetimes. The catalyst formulation methods can include formulation of oxygenate conversion catalysts with binders that are selected from binders having a surface area of roughly 250 m$^2$/g or less, or 200 m$^2$/g or less. In various aspects, during formulation, a weak base can be added to the zeotype crystals, to the binder material, or to the mixture of the zeotype and the binder. It has been unexpectedly discovered that addition of a weak base, so that the weak base is present in at least one component of the binder mixture prior to formulation, can result in longer catalyst exposure lifetimes under methanol conversion conditions.

12 Claims, 4 Drawing Sheets

(51) Int. Cl.
    *B01J 29/70* (2006.01)
    *B01J 21/04* (2006.01)
    *B01J 37/00* (2006.01)

(52) U.S. Cl.
    CPC .............. *C07C 1/20* (2013.01); *B01J 2229/38* (2013.01); *C07C 2529/70* (2013.01)

(56) References Cited

U.S. PATENT DOCUMENTS

| | | | |
|---|---|---|---|
| 3,709,979 | A | 1/1973 | Chu et al. |
| RE29,948 | E | 3/1979 | Dwyer et al. |
| 4,582,815 | A | 4/1986 | Bowes |
| 4,621,161 | A | 11/1986 | Shihabi |
| 6,103,103 | A | 8/2000 | Alexander et al. |
| 9,873,614 | B2 | 1/2018 | Lai |
| 10,099,209 | B2 | 10/2018 | McCarthy et al. |
| 2001/0041162 | A1* | 11/2001 | Schoebrechts ....... C07D 301/12 423/713 |
| 2011/0192766 | A1* | 8/2011 | McCarthy ............ B01J 35/1061 502/64 |
| 2015/0175897 | A1* | 6/2015 | Loveless ................ C10G 3/45 585/408 |
| 2018/0155631 | A1 | 6/2018 | O'Neill et al. |
| 2018/0185827 | A1* | 7/2018 | Cheng ................... C10G 50/00 |

FOREIGN PATENT DOCUMENTS

| | | |
|---|---|---|
| DE | 102016202516 A1 | 8/2016 |
| WO | 20100072716 A1 | 7/2010 |

OTHER PUBLICATIONS

Fathi, et al.; "Improvement of HZSM-5 Performance by Alkaline Treatments: Comparative Catalytic Study in the MTG Reactions"; Fuel, 2014; vol. 116; pp. 529-537 Elsevier Ltd.

The International Search Report and Written Opinion for PCT/US2020/020761 dated May 29, 2020.

Miale, J. N., et al; "Catalysis by Crystalline Aluminosilicates IV Attainable Catalytic Cracking Rate Constants, and Superactivity"; Journal of Catalysis, 1966, vol. 6, pp. 278.

"Superactive Crystalline Aluminosilicate Hydrocarbon Catalysts"; Journal of Catalysis, 1965, vol. 4, pp. 527.

Olson, D. H., et al; "Chemical and Physical Properties of The ZSM-5 Substitutional Series", Journal of Catalysis, 1980, vol. 61, pp. 395.

"Quaternary Ammonium Cation". URL "https://en.wikipedia.org/wiki/Quaternary_ammonium_cation". Nov. 2021.

First Office Action and Search received for Chinese Patent Application No. 202080020347.6, dated Oct. 10, 2022, 19 pages. (English Translation Submitted).

International Preliminary Report on Patentability received for PCT Patent Application No. PCT/US2020/020761, dated Sep. 23, 2021, 8 pages.

* cited by examiner

CATALYST FORMULATION FOR METHANOL CONVERSION CATALYSTS

CROSS REFERENCE TO RELATED APPLICATION

This application claims priority to U.S. Provisional Application Ser. No. 62/818,339 filed Mar. 14, 2019, which is herein incorporated by reference in its entirety.

FIELD

This invention is related to growth and formulation of methanol conversion catalysts with improved catalyst lifetime.

BACKGROUND

A variety of industrial processes are known for conversion of low boiling carbon-containing compounds to higher value products. For example, methanol to gasoline (MTG) is a commercial process that produces gasoline from methanol using ZSM-5 catalysts. In the MTG process, methanol is first dehydrated to dimethyl ether. The methanol and/or dimethyl ether then react in a series of reactions that result in formation of aromatic, paraffinic, and olefinic compounds. The resulting product consists of liquefied petroleum gas (LPG) and a high-quality gasoline comprised of aromatics, paraffins, and olefins. The typical MTG hydrocarbon product consists of 40-50% aromatics plus olefins and 50-60% paraffins.

One difficulty with conventional processes for conversion of methanol to gasoline is that the catalysts can suffer from relatively short effective lifetimes. Due to the nature of the methanol conversion reaction, the catalyst for methanol conversion is prone to having substantial coke formation. While catalyst regeneration can be at least partially effective for restoring catalyst activity, the need for frequent regeneration can increase operating costs and/or reduce throughput in conversion reactor. Thus, it would be beneficial to develop methods that can extend catalyst lifetime under methanol conversion conditions.

SUMMARY OF THE INVENTION

In some aspects, a method for converting an oxygenate feed with an oxygenate conversion catalyst is provided. The method can include exposing a feed comprising oxygenates to an oxygenate conversion catalyst that includes a binder to form a converted effluent. The oxygenate conversion catalyst can correspond to a catalyst formulated with 1.5 wt % to 5.0 wt % of a weak base in the mixture of zeotype and binder during formulation. The feed can be exposed to the oxygenate conversion catalyst under conversion conditions that include an average reaction temperature of 230° C. to 550° C., a total pressure of 10 psig (~70 kPag) to 400 psig (~2800 kPag), and a WHSV of 0.1 $hr^{-1}$ to 10.0 $hr^{-1}$. The conversion catalyst can include the zeotype and 1 wt % to 90 wt % of the binder. The binder can have a surface area of 250 $m^2/g$ or less.

In some aspects, a method for formulating an oxygenate conversion catalyst is provided. The method can include combining a zeotype having oxygenate conversion activity with a binder to form a mixture. The binder can have a surface area of 250 $m^2/g$ or less. The method can further include adding 1.5 wt % to 5.0 wt %, relative to a weight of the mixture, of a weak base to the mixture. The weak base can be added directly to the mixture, or the weak base can be added to the zeotype and/or the binder prior to the combining to form the mixture. Methanol conversion catalyst particles including 1 wt % to 90 wt % binder can then be formed from the mixture.

DETAILED DESCRIPTION

In various aspects, methods are provided for formulation of catalysts with improved catalyst exposure lifetimes under oxygenate conversion conditions. In various additional aspects, methods are described for performing oxygenate conversion reactions using such catalysts with improved catalyst exposure lifetimes. The catalyst formulation methods can include formulation of oxygenate conversion catalysts with binders that are selected from binders having a surface area of roughly 250 $m^2/g$ or less, or 200 $m^2/g$ or less. In various aspects, during formulation, a weak base can be added to the zeotype crystals, to the binder material, or to the mixture of the zeotype and the binder. It has been unexpectedly discovered that addition of a weak base, so that the weak base is present in at least one component of the binder mixture prior to formulation, can result in longer catalyst exposure lifetimes under methanol conversion conditions. Preferably, the weak base can correspond to an organic base.

A methanol conversion catalyst with an increased catalyst lifetime can be valuable in a variety of contexts. For a fixed bed system (such as a trickle bed reactor), increasing the catalyst lifetime can allow for longer run lengths at a given thickness for the catalyst bed and/or similar run lengths with a reduced amount of catalyst. For a system where continuous catalyst regeneration can be performed, such as a fluidized bed reactor or a moving bed reactor, increasing the catalyst lifetime can allow for a reduction in the rate of catalyst removal from the system and corresponding addition of fresh make-up catalyst.

Synthesis and Formulation of Oxygenate Conversion Catalysts

In this discussion and the claims below, a zeotype is defined to refer to a crystalline material having a porous framework structure built from tetrahedra atoms connected by bridging oxygen atoms. Examples of known zeotype frameworks are given in the "Atlas of Zeolite Frameworks" published on behalf of the Structure Commission of the International Zeolite Association", $6^{th}$ revised edition, Ch. Baerlocher, L. B. McCusker, D. H. Olson, eds., Elsevier, New York (2007) and the corresponding web site, http://www.iza-structure.org/databases/. Under this definition, a zeotype can refer to aluminosilicates having a zeolitic framework type as well as crystalline structures containing oxides of heteroatoms different from silicon and aluminum.

Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework. Thus, "zeotypes" as defined herein can include structures such as SAPO and AlPO crystalline frameworks.

A suitable zeotype can correspond to a crystalline material where the largest ring size for the largest pore channel network is greater than a 6-member ring pore size (such as an 8-member, 10-member, or 12-member ring pore channel network). Examples of suitable zeotypes having a 3-dimensional 10-member ring pore channel network include zeotypes having an MFI or MEL framework, such as ZSM-5 or ZSM-11. ZSM-5 is described in detail in U.S. Pat. Nos. 3,702,886 and Re. 29,948. ZSM-11 is described in detail in U.S. Pat. No. 3,709,979. In some aspects, a zeotype with a 3-dimensional pore channel can be preferred for conversion of methanol, such as a zeotype with an MFI framework. More generally, non-limiting examples of suitable frameworks having various dimensionality for the pore channels include framework codes MRE, MTW, TON, MTT, MFI, MEL, BEA, FAU, MWW, and CON. Additionally or alternately non-limiting examples of suitable zeotypes include ZSM-5, ZSM-11, ZSM-12, ZSM-22, ZSM-23, ZSM-48, beta, USY, MCM-22, MCM-36, MCM-49, MCM-56, EMM-10, EMM-13, and CIT-1. Still other examples can correspond to zeotypes that are suitable for methanol to olefin conversion, such as CHA, AEI, and SAPO-34.

In some aspects, it can be beneficial to use a zeotype having a 1-dimensional 10-member ring pore channel network. Examples of suitable zeotypes having a 1-dimensional 10-member ring pore channel network include zeotypes having a MRE (e.g, ZSM-48), MTW (e.g, ZSM-12), TON (e.g., ZSM-22), MTT (e.g., ZSM-23), MOR, and/or MFS (e.g., ZSM-57) framework. Additionally, some higher dimensional framework catalysts, such as zeotypes with 2-dimensional or 3-dimensional pore networks, could potentially also benefit from this approach. Examples of such catalysts include MFI (e.g., ZSM-5), MEL (e.g., ZSM-11), MWW (e.g., MCM-22 and MCM-49), zeolite Y, zeolite L, and BEA (zeolite Beta).

Generally, a zeotype having desired activity for methanol conversion can have a silicon to aluminum molar ratio of 5 to 200, or 15 to 100, or 20 to 80, or 20 to 40. For example, the silicon to aluminum ratio can be at least 10, or at least 20, or at least 30, or at least 40, or at least 50, or at least 60. Additionally or alternately, the silicon to aluminum ratio can be 300 or less, or 200 or less, or 100 or less, or 80 or less, or 60 or less, or 50 or less.

Typically, reducing the silicon to aluminum ratio in a zeotype will result in a zeotype with a higher acidity, and therefore higher activity for cracking of hydrocarbon or hydrocarbonaceous feeds, such as petroleum feeds. However, with respect to conversion of oxygenates, such increased cracking activity may not be beneficial, and instead may result in increased formation of residual carbon or coke during the conversion reaction. Such residual carbon can deposit on the zeotype catalyst, leading to deactivation of the catalyst over time. Having a silicon to aluminum ratio of at least 40, such as at least 50 or at least 60, can reduce or minimize the amount of additional residual carbon that is formed due to the acidic or cracking activity of a catalyst.

It is noted that the molar ratio described above is a ratio of silicon to aluminum. If a corresponding ratio of silica to alumina were described, the corresponding ratio of silica ($SiO_2$) to alumina ($Al_2O_3$) would be twice as large, due to the presence of two aluminum atoms in each alumina stoichiometric unit. Thus, a silicon to aluminum ratio of 10 corresponds to a silica to alumina ratio of 20.

In some aspects, a zeotype in a catalyst can be present at least partly in the hydrogen form. Depending on the conditions used to synthesize the zeotype, this may correspond to converting the zeotype from, for example, the sodium form. This can readily be achieved, for example, by ion exchange to convert the zeotype to the ammonium form followed by calcination in air or an inert atmosphere at a temperature of 400° C. to 700° C. to convert the ammonium form to the active hydrogen form.

Additionally or alternately, a zeotype/zeolitic catalyst can include and/or be enhanced by a transition metal. The transition metal can be any convenient transition metal selected from Groups 6-15 of the IUPAC periodic table. The transition metal can be incorporated into the zeotype/catalyst by any convenient method, such as by impregnation, by ion exchange, by mulling prior to extrusion, and/or by any other convenient method. Optionally, the transition metal incorporated into a zeotype/catalyst can correspond to two or more metals. After impregnation or ion exchange, the transition metal-enhanced catalyst can be treated in air or an inert atmosphere at a temperature of 300° C. to 700° C. The amount of transition metal can be expressed as a weight percentage of metal relative to the total weight of the catalyst (including any zeotype and any binder). A catalyst can include 0.05 wt % to 20 wt % of one or more transition metals, or 0.1 wt % to 10 wt %, or 0.1 wt % to 5 wt %, or 0.1 wt % to 2.0 wt %. For example, the amount of transition metal can be at least 0.1 wt % of transition metal, or at least 0.25 wt % of transition metal, or at least 0.5 wt %, or at least 0.75 wt %, or at least 1.0 wt %. Additionally or alternately, the amount of transition metal can be 20 wt % or less, or 10 wt % or less, or 5 wt % or less, or 2.0 wt % or less, or 1.5 wt % or less, or 1.2 wt % or less, or 1.1 wt % or less, or 1.0 wt % or less.

In various aspects, a catalyst having an extended catalyst lifetime can be formulated by including a weak base, such as an organic base, in the mixture for forming the catalyst particles. The weak base can be added to the zeotype, added to the binder, or added to the mixture of zeotype and binder prior to extrusion, spray drying, or another technique for catalyst particle formation. Examples of suitable weak bases include, but are not limited to, tertiary and quaternary ammonium compounds, such as tetraethylammonium hydroxide. The amount of weak base added during formulation can correspond to 1.5 wt % to 5.0 wt % of the resulting mixture for extrusion, or 2.0 wt % to 5.0 wt %, or 2.5 wt % to 5.0 wt %, or 3.0 wt % to 5.0 wt %.

Suitable binders for zeotype-based catalysts can include various inorganic oxides, such as silica, alumina, zirconia, titania, silica-alumina, cerium oxide, magnesium oxide, yttrium oxide, or combinations thereof. It is noted that relative to many types of binder materials, silica has increased solubility in basic environments. Thus, in some aspects, it can be preferable to use an inorganic oxide with a reduced or minimized content of silica. In such aspects, suitable binders can include alumina, zirconia, cerium oxide, magnesium oxide, yttrium oxide, silica-alumina containing less than 50 wt % silica relative to the weight of the binder, or combinations thereof. Additionally, the suitable binder can have a surface area of 250 $m^2$/g or less, or 200 $m^2$/g or less. It is noted that one method for providing a high surface area binder can be to use a binder with a larger particle size for the individual binder particles. When larger particles are used, the voids between nearest neighbor particles can be increased. Without being bound by any particular theory, it is believed that such larger voids can be beneficial for mitigating the impact of coke formation on the catalyst, thereby providing increased catalyst lifetime.

For catalysts including a binder, the catalyst can comprise at least 10 wt % zeotype, or at least 30 wt %, or at least 50 wt %, such as up to 90 wt % or more. Generally, a binder can be present in an amount between 1 wt % and 90 wt %, for example between 10 wt % and 70 wt % of a catalyst composition, or between 10 wt % and 50 wt %, or between 10 wt % and 40 wt %. In some aspects, the catalyst can include 10 wt % or more of binder, or 20 wt % or more, or 30 wt % or more. Additionally or alternately, the catalyst can include 90 wt % or less of binder, such as 50 wt % or less, or 40 wt % or less, or 35 wt % or less. Combining the zeotype and the binder can generally be achieved, for example, by mulling an aqueous mixture of the zeotype and binder and then extruding the mixture into catalyst pellets. A process for producing zeolite extrudates using a silica binder is disclosed in, for example, U.S. Pat. No. 4,582,815. Optionally, a bound catalyst can be steamed after extrusion.

The catalyst compositions described herein can further be characterized based on activity for hexane cracking, or Alpha value. Alpha value is a measure of the acid activity of a zeotype catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. Higher alpha values correspond with a more active cracking catalyst.

Feedstocks and Products—Oxygenate Conversion

In various aspects, catalysts described herein can be used for conversion of oxygenate feeds to aromatics and/or olefins products, such as oxygenates containing at least one $C_1$-$C_4$ alkyl group and/or other oxygenates. Examples of suitable oxygenates include feeds containing methanol, dimethyl ether, $C_1$-$C_4$ alcohols, ethers with $C_1$-$C_4$ alkyl chains, including both asymmetric ethers containing $C_1$-$C_4$ alkyl chains (such as methyl ethyl ether, propyl butyl ether, or methyl propyl ether) and symmetric ethers (such as diethyl ether, dipropyl ether, or dibutyl ether), or combinations thereof. It is noted that oxygenates containing at least one $C_1$-$C_4$ alkyl group are intended to explicitly identify oxygenates having alkyl groups containing 4 carbons or less. Preferably the oxygenate feed can include at least 30 wt % of one or more suitable oxygenates, or at least 50 wt %, or at least 75 wt %, or at least 90 wt %, or at least 95 wt %. Additionally or alternately, the oxygenate feed can include at least 50 wt % methanol, such as at least 75 wt % methanol, or at least 90 wt % methanol, or at least 95 wt % methanol. In particular, the oxygenate feed can include 30 wt % to 100 wt % of oxygenate (or methanol), or 50 wt % to 95 wt %, or 75 wt % to 100 wt %, or 75 wt % to 95 wt %. In some aspects, a methanol-containing feed can correspond to a feed where the oxygenate percentage corresponds. The oxygenate feed can be derived from any convenient source. For example, the oxygenate feed can be formed by reforming of hydrocarbons in a natural gas feed to form synthesis gas ($H_2$, CO, $CO_2$), and then using the synthesis gas to form methanol (or other alcohols). As another example, a suitable oxygenate feed can include methanol, dimethyl ether, or a combination thereof as the oxygenate.

In addition to oxygenates, in some aspects the feed can also include a co-feed, such as a co-feed including aromatics or olefins. Optionally, in some aspects, the olefins included as part of the feed can correspond to aliphatic olefins that contain 6 carbons or less, so that the olefins are suitable for formation of naphtha boiling range compounds. The olefin portion of the feed can be mixed with the oxygenates prior to entering a reactor for performing oxygenate conversion, or a plurality of streams containing oxygenates and/or olefins can be mixed within a conversion reactor. The feed can include 5 wt % to 40 wt % of olefins (i.e., olefins containing 6 carbons or less), or 5 wt % to 30 wt %, or 10 wt % to 40 wt %, or 10 wt % to 30 wt %. It is noted that the weight percent of olefins in the feed can be dependent on the nature of the olefins. For example, if a $C_5$ olefin is used as the olefin with a methanol-containing feed, the wt % of olefin required to achieve a desired molar ratio of olefin to oxygenate will be relatively high due to the much larger molecular weight of a $C_5$ alkene.

In some aspects, the olefins can correspond to olefins generated during the oxygenate conversion process. In such aspects, a portion of the effluent from the conversion process can be recycled to provide olefins for the feed. In other aspects, the olefins can be derived from any other convenient source. The olefin feed can optionally include compounds that act as inerts or act as a diluent in the conversion process. For example, a stream of "waste" olefins having an olefin content of 5 vol % to 20 vol % can be suitable as a source of olefins, so long as the other components of the "waste" olefins stream are compatible with the conversion process. For example, the other components of the olefin stream can correspond to inert gases such as $N_2$, carbon oxides, paraffins, and/or other gases that have low reactivity under the conversion conditions. Water can also be present, although it can be preferable for water to correspond to 20 vol % or less of the total feed, or 10 vol % or less.

In addition to oxygenates and olefins, a feed can also include diluents, such as water (in the form of steam), nitrogen or other inert gases, and/or paraffins or other non-reactive hydrocarbons. In some aspects, the source of olefins can correspond to a low purity source of olefins, so that the source of olefins corresponds to 20 wt % or less of olefins. In some aspects, the portion of the feed corresponding to components different from oxygenates and olefins can correspond to 1 wt % to 60 wt % of the feed, or 1 wt % to 25 wt %, or 10 wt % to 30 wt %, or 20 wt % to 60 wt %. Optionally, the feed can substantially correspond to oxygenates and olefins, so that the content of components different from oxygenates and olefins is 1 wt % or less (such as down to 0 wt %).

The nature of the products generated from oxygenate conversion can vary widely depending on the conversion conditions and the type of conversion catalyst. In some aspects, such as aspects related to oxygenate conversion to produce gasoline using an MFI or MEL framework catalyst, the yield of aromatics relative to the total hydrocarbon product can be 25 wt % to 60 wt %, or 38 wt % to 60 wt %, or 40 wt % to 52 wt %, or 38 wt % to 45 wt %. The aromatics yield can be lower for a 1-dimensional 10-member ring catalyst, such as an MRE framework catalyst, where the aromatics yield can be 10 wt % to 40 wt %. In various aspects, the yield of olefins relative to the total hydrocarbon product can be 2.0 wt % to 90 wt %, or 2.0 wt % to 70 wt %, or 5.0 wt % to 40 wt %, or 10 wt % to 30 wt %. In various aspects, the yield of paraffins relative to the total hydrocarbon product can be 10 wt % to 45 wt %, or 20 wt % to 35 wt %, or 20 wt % to 45 wt %, or 25 wt % to 40 wt %. Optionally, less than 10 wt % of the paraffins can correspond to $C_1$ paraffins (methane).

The total hydrocarbon product in the conversion effluent can include a naphtha boiling range portion, a distillate fuel boiling range portion, and a light ends portion. Optionally, the conversion effluent can include less than 1.0 wt % of compounds boiling above the distillate fuel boiling range (370° C.+), such as compounds having a final boiling point of 370° C. or less.

In some aspects, the naphtha boiling range portion formed from a conversion process can have a research octane number of 80 or more, or 85 or more, such as up to 90 or possibly still higher. In some other aspects, the naphtha boiling range portion can have a research octane number of 90 or more, or 92 or more, or 94 or more, such as up to 100 or possibly still higher. Research octane number (RON) can be determined according to ASTM D2699.

Suitable and/or effective conditions for performing a conversion reaction can include average reaction temperatures of 230° C. to 550° C. (or 300° C. to 450° C.), total pressures between 1 psig (~7 kPag) to 400 psig (~2800 kPag), or 15 psig (~100 kPag) to 150 psig (~1050 kPag), and an oxygenate space velocity between 0.1 $h^{-1}$ to 10 based on weight of oxygenate relative to weight of catalyst.

Optionally, a portion of the conversion effluent can be recycled for inclusion as part of the feed to the conversion reactor. For example, at least a portion of the light ends from the conversion effluent can be recycled as part of the feed. The recycled portion of the light ends can correspond to any convenient amount of the feed, such as corresponding to 10 wt % to 50 wt % of the total feed to the conversion process. Recycling of light ends can provide olefins, which can serve as an additional reactant in the conversion reaction, as well as providing a mechanism for temperature control.

Various types of reactors can provide a suitable configuration for performing a conversion reaction. Suitable reactors can include fixed bed reactors (such as trickle bed reactors), moving bed reactors, and fluidized bed reactors (such as riser reactors).

Example of Reaction System Configuration

Figure 1:
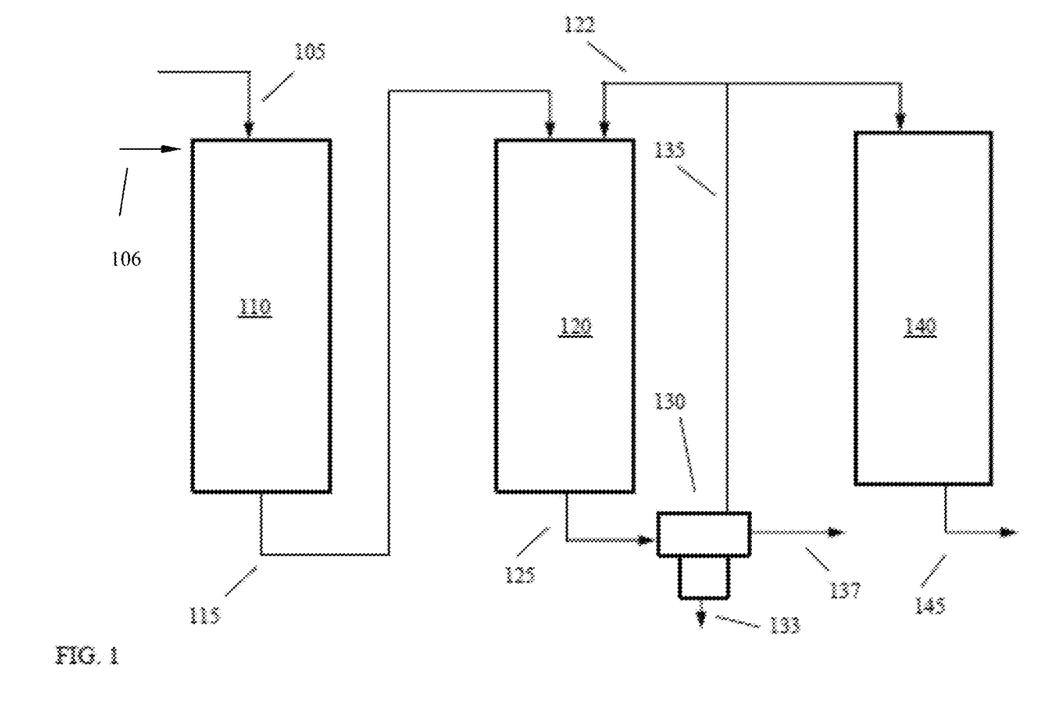
FIG. 1 schematically shows an example of a reaction system for conversion of oxygenates to olefins.

FIG. 1 shows an example of a reaction system configuration for performing oxygenate conversion to form a naphtha boiling range product. It is noted that the reactors shown in FIG. 1 are depicted as fixed bed, downflow reactors (such as trickle-bed reactors) for convenience. It is understood that any or all of the reactors shown in FIG. 1 can alternatively be upflow reactors, moving bed reactors and/or fluidized bed reactors. In FIG. 1, a feed 105 can correspond to an oxygenate-containing feed. In a particular example, feed 105 can correspond to 96 wt % methanol and 4 wt % water. A second (optional) feed 106 can correspond to an olefin-containing feed. Optionally, oxygenate feed 105 can be introduced into a reactor as a plurality of input flows, such as a first input flow containing a mixture of methanol and water and a second input flow containing a mixture of nitrogen and hydrogen. Optionally, oxygenate feed 105 and olefinic feed 106 can be combined prior to entering the reactor 110.

The feed 105 (or alternatively a combination of oxygenate feed 105 and olefinic feed 106) can optionally be introduced into an initial dehydration reactor 110. Initial dehydration reactor 110 can include an acidic catalyst, such as an acidic alumina catalyst, that can facilitate an equilibrium reaction between methanol, water, and dimethyl ether. This can result in production of an effluent 115 that includes both methanol and dimethyl ether. Those of skill in the art will recognize that dimethyl ether and methanol can often be used in similar manners when performing an oxygenate conversion reaction. The dehydration of methanol to form dimethyl ether is highly exothermic. By performing an initial dehydration, the amount of heat generated in the conversion reactor(s) can be reduced, which can allow for improved temperature control in the conversion reactor. Optionally, a portion of the oxygenate feed 105 can bypass the dehydration reactor and can be input directly into conversion reactor 120. In aspects where other oxygenates are used as a feed, such as $C_{2+}$ alcohols or larger ethers, dehydration reactor can be omitted so that feed 105 (or a combination of oxygenate feed 105 and olefinic feed 106) is an input flow for conversion reactor 120.

The oxygenate feed 105 and olefinic feed 106 (and/or the effluent 115 containing both dimethyl ether and methanol) are then passed into conversion reactor 120. The input to conversion reactor 120 can be exposed to a conversion catalyst under effective conditions for forming a conversion effluent 125. The conversion effluent 125 can then be separated, such as by using a 3 phase separator 130. One phase generated by separator 130 can be an aqueous phase 133 that includes a substantial majority of the water present within the conversion effluent 125. Another phase generated by separator 130 can correspond to a hydrocarbon liquid product 137. The hydrocarbon liquid product can correspond to naphtha boiling range compounds formed during the conversion reaction. Optionally, the hydrocarbon liquid product can include a portion of hydrocarbon-like compounds that include one or more heteroatoms, such as oxygen, sulfur, nitrogen, and/or other heteroatoms that are commonly found in petroleum or bio-derived feeds.

A third phase generated by separator 130 can correspond to a hydrocarbon gas product 135. The hydrocarbon gas product 135 can include $C_{4-}$ compounds corresponding to light paraffins and light olefins. Optionally, a recycle portion 122 of hydrocarbon gas product 135 can be recycled as part of the input flows to conversion reactor 120. In some configurations where the amount of recycle portion 122 is sufficiently large, a bleed or waste flow (not shown) can also be present to reduce or minimize the build-up of $C_{4-}$ paraffins in conversion reactor 120. Optionally, a portion of hydrocarbon gas product 135 can be passed onto reactor 140 where it can be converted into a new upgraded product 145.

Example 1—Addition of Weak Base During Catalyst Formulation: ZSM-48

In Example 1, various catalysts were tested in an isothermal fixed-bed reactor without recycle, although recycle is possible and may be desirable as it can further extend catalyst cycle length. This reactor configuration is illustrative and should not be considered limiting. In this example, pure methanol was used as a model feed, but co-feeds such as water, oxygenates, olefins, paraffins, and aromatics are possible and may even be desirable. For the catalysts based on ZSM-48, the conditions for testing included a 2 $h^{-1}$ weight hourly space velocity (WHSV) on a zeotype basis. In other words, the weight of the methanol feed was selected based on the weight of zeotype in the catalyst, and not based on the total weight of the catalyst. Other conditions included a temperature of 450° C., and a pressure of ~100 kPa-g. For the catalysts based on ZSM-5, the conditions tested were a WHSV (zeotype basis) of 6 $h^{-1}$, a temperature of 440° C., and a pressure of ~200 kPa-g.

The first set of catalysts tested corresponded to four different formulations of a ZSM-48 catalyst. The ZSM-48 had a silicon to aluminum ratio of ~140 and an Alpha value of ~120. One catalyst formulation corresponded to a binderless formulation. The other formulations corresponded to formulations where the resulting extruded catalyst particles included approximately 80 wt % of the ZSM-48 and 20 wt % of the binder. A first binder corresponded to Versal-300 alumina, which is an alumina with a surface area of 300 m$^2$/g or more. The second binder corresponded to a Catapal alumina binder, with a surface area of 200 m$^2$/g or less. A third binder corresponded to a yttria binder, with a surface area of 100 m$^2$/g or less.

Figure 2:
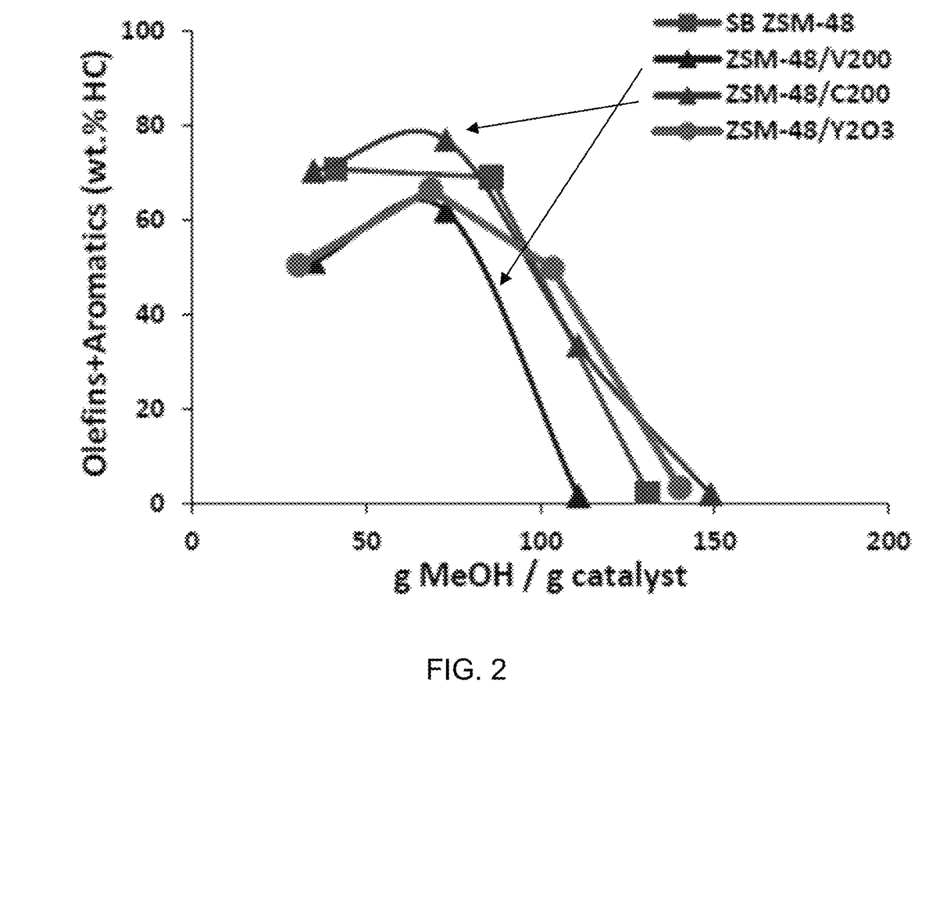
FIG. 2 shows combined olefin plus aromatics yield versus the amount of methanol exposure per amount of catalyst for ZSM-48 catalysts formulated without inclusion of a weak base.
Figure 3:
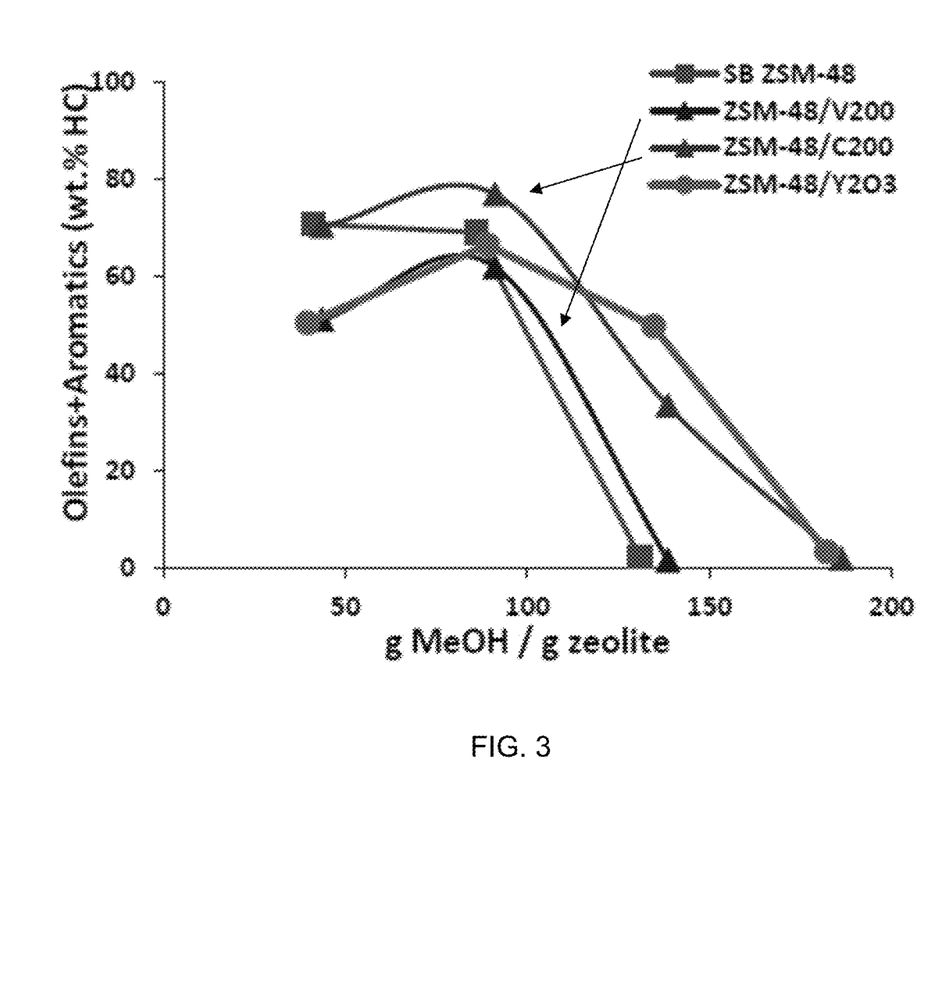
FIG. 3 shows combined olefin plus aromatics yield versus the amount of methanol exposure per amount of zeotype for ZSM-48 catalysts formulated without inclusion of a weak base.

For the catalysts including a binder, the catalysts shown in FIG. 2 and FIG. 3 corresponded to catalysts formulated with binder in a conventional manner, so that no additional weak base was included in the zeotype/binder mixture prior to extrusion.

FIG. 2 shows results from exposing the methanol feed to the self-bound catalyst and the bound catalysts where a weak base was not included. The results shown in FIG. 2 correspond to the combined yield of olefins and aromatics relative to the amount of methanol the catalyst has been exposed to (grams of methanol per gram of catalyst). As shown in FIG. 2, all of the catalysts appear to have a maximum in yield around roughly 75 g MeOH/g catalyst. The yield then starts to decline. The catalyst bound with the high surface area alumina goes to a yield of substantially 0 at roughly 100 g MeOH/g catalyst. The self-bound catalyst goes to a yield of substantially 0 at roughly 130 g MeOH/g catalyst. The catalysts bound with the lower surface area binders have longer lifetimes between roughly 140 and 150 g MeOH/g catalyst.

In FIG. 3, the same data is displayed relative to FIG. 2, but the horizontal axis is different. In FIG. 3, the horizontal axis represents the grams of methanol exposed to the catalyst relative to the grams of zeotype in the catalyst. By contrast, the horizontal axis in FIG. 2 shows the grams of methanol exposed to the catalyst relative to the grams of catalyst (including any binder). The data in FIG. 3 shows that on a grams of methanol per grams of zeotype basis, the catalyst with a binder having a surface area of 300 m$^2$/g or more had roughly the same activity versus amount of exposure as the catalyst formulated without a binder. The catalysts formulated with binders having surface areas of 250 m$^2$/g or less, however, appeared to have higher activity per amount of exposure relative to the binderless catalyst.

Figure 4:
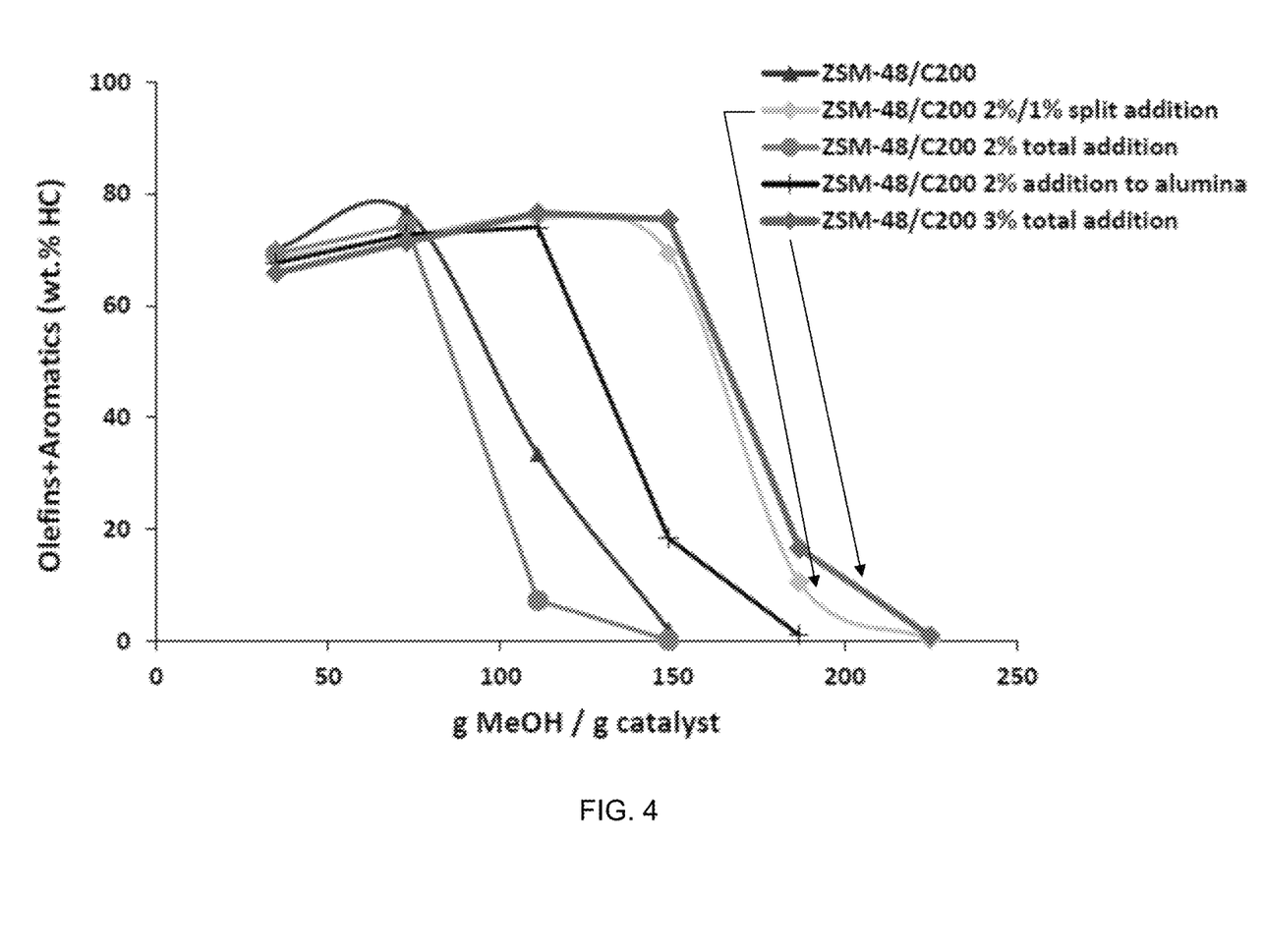
FIG. 4 shows combined olefin plus aromatics yield versus the amount of methanol exposure per amount of catalyst for ZSM-48 catalysts formulated with inclusion of a weak base.

The results shown in FIG. 2 and FIG. 3 illustrate that the surface area of the binder can impact the exposure lifetime of a zeolitic catalyst for methanol conversion. It has been discovered that use of a low surface area binder can unexpectedly provide further enhancement of the exposure lifetime when a weak base is incorporated into the mixture for forming the bound catalyst. FIG. 4 shows results for various ZSM-48 catalysts formulated with a binder having a surface area of 100 m$^2$/g or less (Catapal-200 alumina). One catalyst shown in FIG. 4 corresponded to a catalyst that was formulated without inclusion of a weak base. A second catalyst corresponded to addition of 2 wt % of a weak base (TEAOH) to the alumina, followed by addition of another 1 wt % of the weak base to the combined zeotype and binder mixture prior to extrusion. A third catalyst corresponded to addition of 2 wt % of the weak base to the combined zeotype and binder mixture. A fourth catalyst corresponded to addition of 2 wt % of the weak base to the alumina. A fifth catalyst corresponded to addition of 3 wt % of the weak base to the combined zeotype and binder mixture prior to extrusion.

As shown in FIG. 4, addition of 3 wt % or more of the weak base prior to forming the catalyst resulted in an unexpected increase in the amount of methanol that can be exposed to a catalyst prior to a reduction in activity for forming olefins and/or aromatics. This unexpected increase in exposure lifetime did not appear to result in an increase in the peak selectivity for formation of aromatics and olefins. Instead, the amount of exposure time where the catalyst provided roughly the peak selectivity for formation of olefins plus aromatics was extended. It is noted that for addition of 2 wt % of weak base, a partial improvement in exposure lifetime was observed when the weak base was added to just the alumina, which corresponded to only 20 wt % of the final catalyst particles.

Example 2—Addition of Weak Base During Catalyst Formulation: ZSM-5

Additional characterization of the impact of addition of a weak base (TEAOH) during catalyst formulation was performed using catalysts including 65 wt % of ZSM-5 and 35 wt % of the Catapal-200 alumina as a binder (surface area of less than 100 m$^2$/g). The test conditions (as described above in Example 1) were believed to be representative of suitable conditions for conversion of methanol to gasoline. Catalyst exposure lifetime was determined based on the time required for the concentration of unconverted methanol in the aqueous phase to reach 1%. Under a first test conditions, a catalyst formulated without addition of TEAOH had an exposure lifetime of 4.8 days. Under a second test condition, a catalyst formulated by adding 3.0 wt % of the weak base to the alumina resulted in an exposure lifetime of 5.1 days. In a third test condition, a catalyst formulated with addition of 3.0 wt % TEAOH to the combined zeotype and binder mixture had a lifetime of 5.9 days.

Without being bound by any particular theory, one possible explanation for the improved catalyst lifetime may be due to a reduction of sites on the binder surface that are suitable for catalyzing unwanted side reactions. Such unwanted side reactions could correspond to reactions that form coke-precursors, such as formaldehyde or acetic acid. To further investigate this, alumina particles treated with various amounts of TEAHO were characterized based on $CO_2$ adsorption using thermal gravimetric analysis (TGA). The alumina particles were formed using the Catapal-200 alumina that had a surface area of less than 100 m$^2$/g. Table 1 shows the amount of $CO_2$ released during the analysis. The results in Table 1 include a comparative alumina (no TEAOH addition); alumina particles where the TEAOH was added to the alumina by impregnation after formation of the alumina particles; and alumina particles where the TEAOH was added to the alumina in a muller, followed by extrusion of the alumina particles.

TABLE 1

| $CO_2$ Desorption from Alumina Particles | | |
|---|---|---|
| Addition Method | TEAOH (Wt %) | $CO_2$ Desorption (umol/g) |
| <comparative> | None | 465 |
| Impregnation | 1.0 | 397 |
| Impregnation | 2.0 | 399 |
| Impregnation | 4.0 | 367 |

TABLE 1-continued

CO₂ Desorption from Alumina Particles

| Addition Method | TEAOH (Wt %) | CO$_2$ Desorption (umol/g) |
| --- | --- | --- |
| Added to Extrusion Mixture | 0.9 | 440 |
| Added to Extrusion Mixture | 1.0 | 420 |
| Added to Extrusion Mixture | 2.0 | 398 |
| Added to Extrusion Mixture | 3.0 | 371 |

As shown in Table 1, addition of TEAOH to the alumina either prior to extrusion to form particles or after formation of particles resulted in a reduction in the amount of desorbed $CO_2$. This is believed to indicate that the addition of weak base can be performed either during or after the formulation process.

ADDITIONAL EMBODIMENTS

Embodiment 1

A method for converting an oxygenate feed with an oxygenate conversion catalyst, comprising: exposing a feed comprising oxygenates to an oxygenate conversion catalyst at an average reaction temperature of 230° C. to 550° C., a total pressure of 10 psig (~70 kPag) to 400 psig (~2800 kPag), and a WHSV of 0.1 hr$^{-1}$ to 10.0 hr$^{-1}$, to form a converted effluent, the conversion catalyst comprising a zeotype and 1 wt % to 90 wt % of a binder, the binder having a surface area of 250 m$^2$/g or less, wherein the oxygenate conversion catalyst comprises a catalyst formulated with 1.5 wt % to 5.0 wt % of a weak base in the mixture of zeotype and binder during formulation.

Embodiment 2

The method of Embodiment 1, wherein the oxygenate conversion catalyst comprises a catalyst formulated with 2.0 wt % to 5.0 wt % of a weak base in the mixture of zeotype and binder during formulation.

Embodiment 3

The method of any of the above embodiments, wherein the oxygenate comprises 90 wt % or more of methanol, dimethyl ether, or a combination thereof.

Embodiment 4

The method of any of the above embodiments, wherein the feed further comprises olefins.

Embodiment 5

The method of any of the above embodiments, wherein the conversion effluent comprises a $C_{5+}$ fraction having an octane rating of 80 or more (or 90 or more).

Embodiment 6

A method for formulating an oxygenate conversion catalyst, comprising: combining a zeotype having oxygenate conversion activity with a binder to form a mixture, the binder having a surface area of 250 m$^2$/g or less; adding 1.5 wt % to 5.0 wt %, relative to a weight of the mixture, of a weak base to the mixture; and forming oxygenate conversion catalyst particles comprising 1 wt % to 90 wt % binder from the mixture.

Embodiment 7

The method of Embodiment 6, wherein forming the oxygenate conversion catalyst particles comprises extruding the oxygenate conversion catalyst particles; or wherein forming the oxygenate conversion catalyst particles comprises spray drying the oxygenate conversion catalyst particles; or wherein forming the oxygenate conversion catalyst particles to comprises forming beads of the oxygenate conversion catalyst particles.

Embodiment 8

The method of Embodiment 6 or 7, wherein adding the weak base to the mixture comprises adding at least a portion of the weak base to the zeotype prior to the combining, or wherein adding the weak base to the mixture comprises adding at least a portion of the weak base to the binder prior to the combining, or a combination thereof.

Embodiment 9

The method of any of Embodiments 6 to 8, wherein adding the weak base to the mixture comprises adding 2.0 wt % to 5.0 wt % of the weak base to the mixture.

Embodiment 10

The method of any of the above embodiments, wherein the weak base comprises an organic base, a quaternary ammonium base, a tertiary ammonium base, a diquaternary ammonium base, tetraethylammonium hydroxide, or a combination thereof.

Embodiment 11

The method of any of the above embodiments, wherein the binder comprises a binder with a surface area of 200 m$^2$/g or less.

Embodiment 12

The method of any of the above embodiments, wherein the binder comprises alumina, silica, cerium oxide, magnesium oxide, titania, yttria, silica-alumina, or a combination thereof; or wherein the binder comprises alumina, cerium oxide, magnesium oxide, titania, yttria, or a combination thereof.

Embodiment 13

The method of any of the above embodiments, wherein the oxygenate conversion catalyst further comprises 0.1 wt % to 3.0 wt % of a transition metal.

Embodiment 14

An oxygenate conversion catalyst made according to any of Embodiments 6-13.

All numerical values within the detailed description and the claims herein are modified by "about" or "approximately" the indicated value, and take into account experimental error and variations that would be expected by a person having ordinary skill in the art.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for converting an oxygenate feed with an oxygenate conversion catalyst, comprising:
    exposing a feed comprising oxygenates to an oxygenate conversion catalyst at an average reaction temperature of 230° C. to 550° C., a total pressure of 10 psig (~70 kPag) to 400 psig (~2800 kPag), and a WHSV of 0.1 $hr^{-1}$ to 10.0 $hr^{-1}$, to form a converted effluent, the conversion catalyst comprising conversion catalyst particles, the conversion catalyst particles comprising a zeotype and 1 wt % to 90 wt % of a binder, the binder having a surface area of 250 $m^2/g$ or less,
    wherein the oxygenate conversion catalyst comprises conversion catalyst particles formulated with 2.5 wt % to 5.0 wt % of an organic base in a mixture of zeotype and binder during formulation, the organic base being present in the mixture during formation of catalyst particles from the mixture,
    wherein the zeotype is ZSM-48, and
    wherein the organic base comprises a quaternary ammonium base, a tertiary ammonium base, a diquaternary ammonium base, or a combination thereof.

2. The method of claim 1, wherein the binder comprises a binder with a surface area of 200 $m^2/g$ or less.

3. The method of claim 1, wherein the binder comprises a median particle size of 20 μm or more.

4. The method of claim 1, wherein the binder comprises alumina, silica, cerium oxide, magnesium oxide, titania, yttria, silica-alumina, or a combination thereof.

5. The method of claim 1, wherein the binder comprises alumina, cerium oxide, magnesium oxide, titania, yttria, or a combination thereof.

6. The method of claim 1, i) wherein the oxygenate comprises 90 wt % or more of methanol, dimethyl ether, or a combination thereof; ii) wherein the feed further comprises olefins, aromatics, or a combination thereof or iii) a combination of i) and ii).

7. The method of claim 1, wherein the conversion effluent comprises a $C_{5+}$ fraction having an octane rating of 80 or more.

8. The method of claim 1, wherein the oxygenate conversion catalyst further comprises 0.1 wt % to 3.0 wt % of a transition metal.

9. The method of claim 1, wherein the oxygenate conversion catalyst comprises a catalyst formulated with 3.0 wt % to 5.0 wt % of the organic base in the mixture of zeotype and binder during formulation.

10. The method of claim 1, wherein the organic base is added prior to extrusion, spraying draying or another technique for catalyst particle formation.

11. The method of claim 1, wherein adding the organic base to the mixture comprises adding at least a portion of the organic base to the zeotype prior to the formulation, or wherein adding the organic base to the mixture comprises adding at least a portion of the organic base to the binder prior to the formulation, or a combination thereof.

12. The method of claim 1, wherein the organic base comprises tetraethyl ammonium hydroxide.

* * * * *